US012594556B2

(12) United States Patent
Coppeta et al.

(10) Patent No.: US 12,594,556 B2
(45) Date of Patent: Apr. 7, 2026

(54) METHOD AND DEVICE FOR HIGH FIELD STRENGTH ELECTROTRANSFECTION OF MICROVESCICLES AND CELLS

(71) Applicant: The Charles Stark Draper Laboratory, Inc., Cambridge, MA (US)

(72) Inventors: Jonathan R. Coppeta, Windham, NH (US); Timothy J. Biliouris, Brighton, MA (US); Daniel F. King, Watertown, MA (US); Vishal Tandon, Somerville, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 18/515,386

(22) Filed: Nov. 21, 2023

(65) Prior Publication Data

US 2024/0131513 A1 Apr. 25, 2024

Related U.S. Application Data

(62) Division of application No. 16/560,707, filed on Sep. 4, 2019, now Pat. No. 11,878,300.

(Continued)

(51) Int. Cl.
| | |
|---|---|
| *B01L 3/00* | (2006.01) |
| *C12N 13/00* | (2006.01) |
| *C12N 15/87* | (2006.01) |

(52) U.S. Cl.
CPC ..... *B01L 3/502715* (2013.01); *B01L 3/50273* (2013.01); *C12N 13/00* (2013.01);
(Continued)

(58) Field of Classification Search
CPC ......... C12M 1/42; C12M 41/40; C12N 13/00; C12N 15/87; B01L 2300/0645;
(Continued)

(56) References Cited

U.S. PATENT DOCUMENTS

| | | | |
|---|---|---|---|
| 2007/0105206 A1 | 5/2007 | Lu et al. | |
| 2010/0203521 A1* | 8/2010 | Klapperich | ............. C01B 32/15 |
| | | | 435/6.13 |

(Continued)

FOREIGN PATENT DOCUMENTS

| | | |
|---|---|---|
| CN | 107988070 | 5/2018 |
| EP | 3296388 A1 | 3/2018 |

OTHER PUBLICATIONS

Alvarez-Erviti, L., et al., "Delivery of siRNA to the mouse brain by systemic injection of targeted exosomes," Nature Biotechnology, 29(4): 341-347 (2011).

(Continued)

*Primary Examiner* — Dean Kwak
(74) *Attorney, Agent, or Firm* — Wolf, Greenfield & Sacks, P.C.

(57) ABSTRACT

A device, system and process involve conducting electroporation of microvesicles or exosomes or other target structures in a microfluidic arrangement at pressures that exceed atmospheric pressure. Single as well as multiple flow configurations can be employed. In some cases, the system and its operation are computer-controlled for partial or complete automation.

18 Claims, 7 Drawing Sheets

Related U.S. Application Data

(60) Provisional application No. 62/726,691, filed on Sep. 4, 2018.

(52) U.S. Cl.
CPC ...... *C12N 15/87* (2013.01); *B01L 2200/0647* (2013.01); *B01L 2300/06* (2013.01); *B01L 2300/0645* (2013.01); *B01L 2300/0809* (2013.01); *B01L 2400/0421* (2013.01); *B01L 2400/0424* (2013.01)

(58) Field of Classification Search
CPC ....... B01L 3/502715; B01L 2200/0647; B01L 3/50273; B01L 2300/047; B01L 2300/06; B01L 2300/0809; B01L 2300/14; B01L 2400/0421; B01L 2400/0424; B01L 2400/0496; B01L 3/5027; B01L 3/502753
See application file for complete search history.

(56) References Cited

U.S. PATENT DOCUMENTS

| | | |
|---|---|---|
| 2015/0276727 A1 | 10/2015 | Talebpour et al. |
| 2018/0016535 A1 | 1/2018 | Levner et al. |
| 2018/0016539 A1* | 1/2018 | Ding ..................... C12M 35/04 |
| 2019/0292510 A1* | 9/2019 | Tandon ................. C12N 15/87 |
| 2019/0292565 A1 | 9/2019 | Tandon et al. |
| 2019/0338235 A1 | 11/2019 | Coppeta et al. |
| 2020/0071727 A1 | 3/2020 | Tandon et al. |

OTHER PUBLICATIONS

Kelly, A.E., et al., "Low-Conductivity Buffers for High-Sensitivity NMR Measurements,", J. Am. Chem. Soc., 124(40), 12013-12019 (2002).

Kotnik, T., et al., "Analytical Description of Transmembrane Voltage Induced by Electric Fields on Spheroidal Cells," Biophysical Journal, 79(2): 670-679 (2000).

Pucihar, G., et al. "The influence of medium conductivity on electropermeabilization and survival of cells in vitro," Bioelectrochemistry, 54: 107-115 (2001).

Wahlgren, J., et al., "Plasma exosomes can deliver exogenous short interfering RNA to monocytes and lymphocytes," Nucleic Acids Research, 40(17): e130 (2012).

Partial Search Report of the International Searching Authority, mailed on May 18, 2020, from International Application No. PCT/US2019/049564, filed on Sep. 4, 2019. 14 pages.

Database WPI Thomas Scientific, London, GB; AN 2018-393839 XP-002798930 (2017).

International Search Report and Written Opinion of the International Searching Authority, mailed on Jul. 9, 2020, from International Application No. PCT/US2019/049564, filed on Sep. 4, 2019. 17 pages.

International Preliminary Report on Patentability, mailed on Mar. 18, 2021, from International Application No. PCT/US2019/049564, filed on Sep. 4, 2019. 10 pages.

* cited by examiner

METHOD AND DEVICE FOR HIGH FIELD STRENGTH ELECTROTRANSFECTION OF MICROVESCICLES AND CELLS

RELATED APPLICATIONS

This application is a Divisional of U.S. application Ser. No. 16/560,707, filed on Sep. 4, 2019, which claims the benefit under 35 USC 119(e) of U.S. Provisional Application No. 62/726,691, filed on Sep. 4, 2018, both of which are incorporated herein by reference in their entirety.

BACKGROUND OF THE INVENTION

Many applications in biology, medicine, pharmaceutical research and other areas use techniques in which genetic materials are introduced into cells. The term "transformation" is often used when working with bacteria or non-animal eukaryotic cells, including plant cells. "Transduction" requires virus-mediated gene transfer into eukaryotic cells, while "transfection" refers to gene delivery by means other than a virus (chemical transfer, electrotransfer, etc).

Biological materials of interest include not only DNA, siRNA, mRNA, RNP complexes, but also small molecules or proteins such as antibodies. In many cases, the process involves opening transient pores or "holes" in the cell membrane to allow the uptake of the "cargo" material and thus alter or genetically modify the cells or cell products.

One common technique used to temporarily permeabilize cells, typically by applying an electric pulse, is electroporation. Parameters considered when developing electroporation procedures include cell properties (cell size, shape, membrane structure, surface charge, for example), the cell environment, and attributes of the applied electric field, (e.g., pulse intensity, number of pulses, pulse duration, pulse shape and/or frequency). It is generally believed that membrane permeabilization during electroporation occurs after the applied electric field induces a threshold value in the transmembrane potential or "electroporation threshold" and that, at a given applied electric field, there is a threshold for the number of pulses and pulse length, needed for successful electroporation. The Schwan equation and related derivations are often used to estimate a cell's transmembrane potential that develops in response to relevant experimental parameters including applied field, cell size, conductivities of media, cellular cytosol, and cell membrane, and membrane thickness ("Analytical Description of Transmembrane Voltage Induced by Electric Fields on Spheroidal Cells", Biophysical Journal Volume 79 August 2000 670-679).

Attractive for potential uses in prognosis, therapy, or as biomarkers, exosomes are cell-derived vesicles that are present in many if not all eukaryotic fluids, including blood, urine, as well as cell culture media. Generally, exosomes are composed of lipid bilayer membranes with multiple adhesive proteins on their surface. Known for their cell-to-cell communication characteristics, it is thought that exosomes may find applications in targeted cell therapy.

Whereas eukaryotic cells typically have a diameter within the range of from about 10 to about 100 microns ($\mu$m), typical microvesicles and exosome diameters are between 30 and 1000 nanometers (nm). At such reduced dimensions, exosomes are also smaller than most prokaryotic cells (0.1-5.0 $\mu$m in diameter).

Various electroporation devices have been developed and are commercially available. However, they are generally designed and/or optimized for prokaryotic and/or eukaryotic cells.

It is generally believed that existing electroporation systems cannot achieve the field strengths thought to be required for exosome electroporation; approximately 100-300 kV/cm predicted by the Schwan equation. Although some academic papers (see, e.g., Nucleic Acids Research, 2012, Vol. 40, No. 17 e130, or "Delivery of siRNA to the mouse brain by systemic injection of targeted exosomes", Nature Biotechnology, 20 Mar. 2011, doi:10.1038/nbt.1807) appear to indicate loading of exosomes at low field strengths (~1-10 kV/cm), it is uncertain if luminal loading was actually achieved in these studies. It is hypothesized that luminal loading would protect the therapeutic agent from in vivo degradation mechanisms, and allow for a higher precision delivery method.

SUMMARY OF THE INVENTION

Attempting to apply existing electroporation approaches to exosomes raises various difficulties. One major impediment relates to physical differences in the relevant length scales for electroporation, with cellular diameters spanning a range several orders of magnitude larger than exosomes. Assuming the Schwan equation ("Analytical Description of Transmembrane Voltage Induced by Electric Fields on Spheroidal Cells", Biophysical Journal Volume 79 August 2000 670-679) is a valid model of transmembrane potential, exosome equivalent transmembrane potentials are not accessible with commercially available electroporation systems. Specifically, high field strengths of 100-300 kV/cm are required to achieve transmembrane potentials in the 0.2 to 1 Volt range and variable pulse lengths (10 nanoseconds-1,000 microseconds) may be targeted.

In addition, commercially available electroporation devices expose biologics to direct contact with electrodes, resulting in potential damage due to local heating and Faradaic by-products (hydronium ions, hydroxyl ions, chlorine, free radicals, and electrode breakdown by-products (e.g. aluminum ions and particulate)). Existing electroporation approaches lack microfluidics to transport heat away from thermally susceptible biological entities. They also lack co-localization of exosomes and payload, leading to inefficient use of payload. Absent too is a high throughput of transfection.

A need exists, therefore, for equipment and procedures that target and/or facilitate the electroporation of exosomes. A need also exists for approaches that address one or more of the deficiencies discussed above.

Generally, the invention relates to transferring (uploading or unloading) materials into or out of target structures such as, for instance, exosomes, other vesicles or even cells. In specific aspects, permeabilization of the target structures is conducted by electroporation techniques in a system that includes a stream containing the target structures under pressures exceeding atmospheric pressures and generally at field strengths above the dielectric breakdown strength of the same fluid under atmospheric pressures.

Flow patterns can be supported by microchannels and, in some embodiments, the invention relates to a device designed to direct flows such as those described above through an electric field. Additionally, or alternatively, the device provides an individual inlet and corresponding outlet for each flow. In one example, separate inlets/outlets are provided for directing the central flow, a first inner sheath flow, a second inner sheath flow, a first outer sheath flow and a second outer sheath flow.

Practicing the invention facilitates the electroporation of exosomes and addresses problems encountered with conventional systems. Robust, flexible and versatile, embodiments of the invention can be applied or adapted to materials other than exosomes, cells or other vesicles, for instance. Principles described herein also can be employed to remove some or all of the contents of target structures; that is, opening pores and allowing the internal contents to diffuse out either passively or via active electrophoretic forces.

In general, according to one aspect, the invention features an electroporation system. The system comprises an electroporation device comprising a flow channel and a pumping system for generating controlled pressures and flow rates through the flow channel undergoing electroporation. The pressure are elevated, exceeding two atmospheres.

In some cases, the pressures are higher than 100 pounds per square inch or 690 kPa, or higher than 1000 pounds per square inch or 6900 kPa, or higher than 2000 pounds per square inch or 13800 kPa.

In a current example, the pumping system comprises a syringe pump. A HPLC (High Pressure Liquid Chromatography) pump could also be used.

A receiver device is used to control back pressure in the flow channel.

In a current example, the electroporation device comprises a top block, a bottom block, and a dielectric spacer separating the top block and the bottom block. Typically, the blocks have a thickness that is greater than 5 millimeters to provide adequate rigidity. The spacer preferably comprises a flow channel cutout in the spacer for defining lateral sides of the flow channel. A profile of the flow channel can be narrow at each end with a wider center.

In general, according to another aspect, the invention features an electroporation device comprising a top block, a bottom block, and a dielectric spacer separating the top block and the bottom block and having a flow channel cutout for defining lateral sides of a flow channel.

In general, according to another aspect, the invention features an electroporation method comprising providing a flow channel, generating pressures of greater than two atmospheres in the flow channel, and electroporating targets, such as microvesicles or exosomes, in the flow channel.

In general, according to another aspect, the invention features an electroporation system comprising a receiving device providing a backpressure in a flow channel, an input device for pumping a fluid containing targets into the flow channel at a desired flow rate, and an electroporation device for electroporating targets in the flow channel.

In general, according to another aspect, the invention features an electroporation method comprising providing a backpressure at a flow channel, pumping a fluid containing targets into the flow channel at a desired flow rate, and an electroporation of targets in the flow channel.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1A:
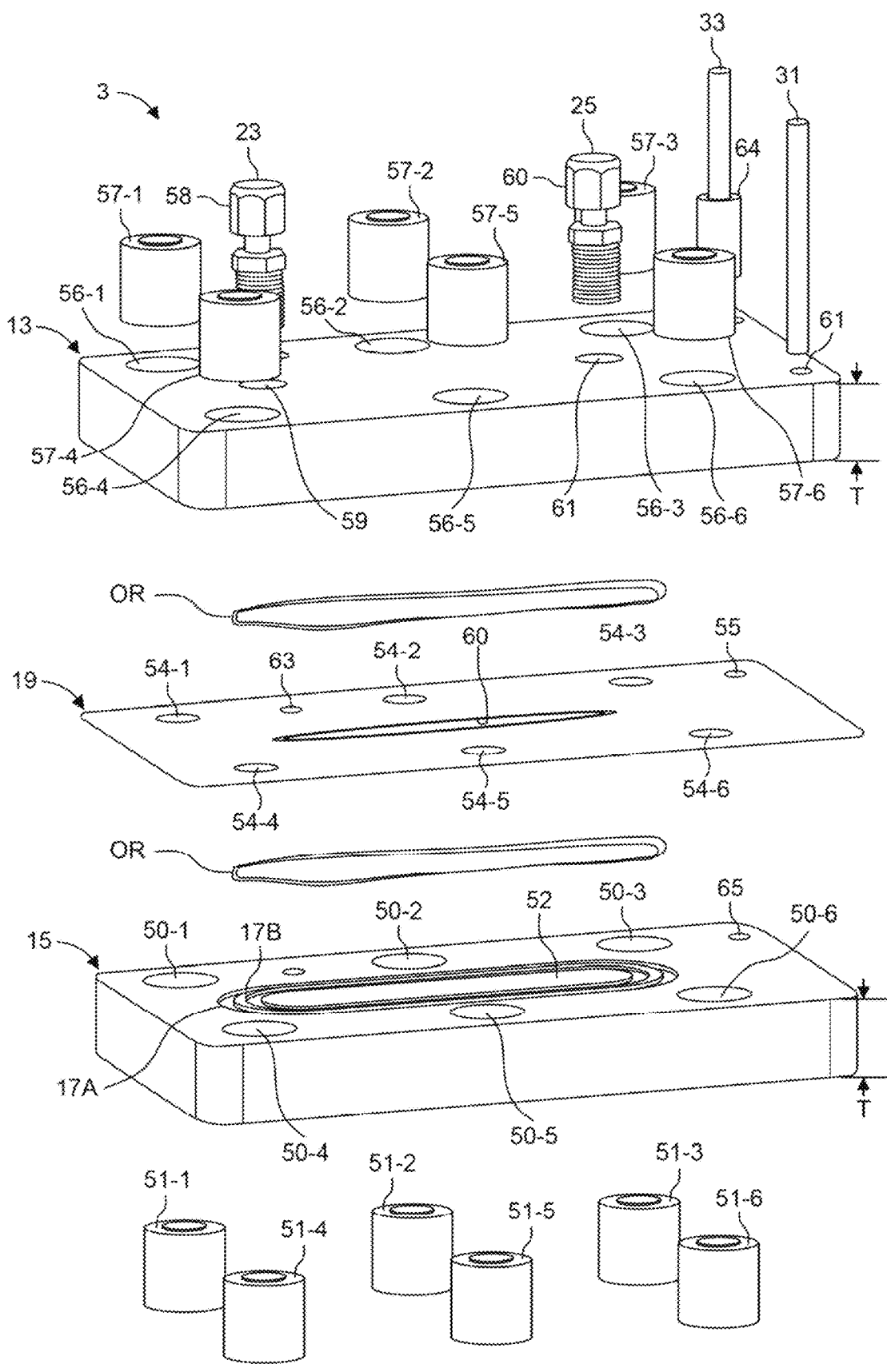
FIGS. 1A and 1B are a perspective exploded view and a perspective view of an electroporation device for a single flow according to the present invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention generally relates to approaches for transferring one or more material(s), referred to herein as "cargo" or "payload", into or out of target structures (also referred to herein as "targets"). Specific aspects relate to microfluidic techniques suitable for the electroporation of vesicles such as microvesicles and exosomes, for instance. Other target structures that can be used include various cell types as well as other materials that can be loaded with cargo via electroporation techniques.

The target structures can be characterized by their size. Some have a diameter that is less than or equal to about 100 nm, for instance within the range of from about 30 to about 1000 nm. Other suitable targets have a diameter that is within the range of from about 10 to about 100 μm. In further cases, the target structures have a diameter within the range of from about 0.1 to about 5.0 μm.

In many embodiments the target is nanoparticles, i.e., vesicles having a diameter equal or less than 100 nanometers (nm), such as, for example, within the range of from about 30 to about 100 nm. In other embodiments, the target is a microparticle, e.g., a cell, having a diameter greater than about 100 nm. In many cases, the microparticle can have a diameter of up to 25, 50, 75, or 100 μm. T-cells, a common target for electroporation transfection, for example, range in size from about 6 μm to 12 μm.

The targets can be provided in a suitable buffer, as known in the art or as developed for a particular application. This buffer can be referred to as the targets' "preferred" buffer. Examples include but are not limited to commercially available buffers such as BTX Cytoporation T-media and those known in the literature such as "Low-Conductivity Buffers for High-Sensitivity NMR Measurements", J. AM. CHEM. SOC. 2002, 124, 12013-12019, "The influence of medium conductivity on electropermeabilization and survival of cells in vitro", Bioelectrochemistry 54 Ž2001. 107-115.

The cargo is a suitable material that can be incorporated into the targets. Examples include but are not limited to small molecules, chromosomes, DNA, RNA, RNP's e.g., mRNA, siRNA, gRNA, ssRNA, Crisper Cas9), other genetic materials, oligomers, biomarkers, proteins, transposons, biomolecule complexes, small molecules, therapeutic agents, and so forth. In one illustrative example siRNA is loaded into exosomes as a cancer therapy to knock down oncogenes in vivo.

Cargo to be introduced in the targets can be provided in one or more electroporation buffers or solutions. Many cargo-containing buffers are commercially available. In some cases, a suitable solution can be prepared using, for example, techniques and ingredients known in the art.

In further implementations, principles described herein are applied or adapted to removing some or all of the contents from the targets, vesicles, for instance. In this situation, opening the vesicle pores allows the internal contents to diffuse out either passively or via active electrophoretic forces. Releasing contents from the targets may be particularly useful with cargo that is insufficiently characterized, thus raising potential regulatory or other concerns during therapeutic development.

In many of its aspects, the invention relates to permeabilizing target structures such as microvesicles, cells, exosomes or other membrane bound structures in a device or system in which the target structures are present in a fluid flow or stream at a pressure greater than the atmospheric pressure. In general, microvesicles are a type of extracellular vesicle that are released from the cell membrane and reside in the interstitial space between cells and in many types of body fluids including blood. Microvesicles range in size from 30 nanometers (nm) in diameter to 1000 nm in diameter. Microvesicles are generally larger, on average, than exosomes, which range in size from about 30 nm to about 200 nm.

A device for a single flow configuration (in which target structures can be provided in a suitable buffer) is illustrated in FIGS. 1A (exploded view) and 1B. In this configuration, two blocks form the top wall and the bottom wall of a flow channel and electroporation electrodes, respectively.

In more detail, the electroporation device (also referred to herein as "electroporation chamber") 3 includes top plate or block 13 and bottom plate or block 15, which can be formed of conductive metals that are biocompatible and bio-inert or conductive metals that are coated with a biocompatible bio-inert metal. Examples of biocompatible bio-inert metals include platinum, stainless steel (316 stainless steel, for example), nitinol (a metal alloy of nickel and titanium), and cobalt-chrome. Examples of structural materials that could be coated with biocompatible bio-inert coatings include, copper and aluminum. Other materials such as rigid plastics (Ultem, PEEK, COC), ceramics, glass, or silicon that have a conductive metal coating may also be used to construct block 13 and 15. In some cases, it may be advantageous to make the structural block from a transparent material to visualize the flow.

Usually, each of the blocks must be rigid to withstand the generated pressures. As a result, in many embodiments, each of the blocks is metal and has a thickness T that is greater than 5 millimeters.

Two O-ring grooves 17A, 17B are formed in the bottom block 15 and seat either a single or concentric O-rings OR to enable high fluidic pressure sealed operation. A single O-ring can be employed in some embodiments.

In the illustrate example, six (6) holes 50-1 to 50-6 surround the O-ring grooves 17A, 17B. These holes 50-1 to 50-6 receive respective clamping bolts. The holes 50-1 to 50-6 of the top block 13 are sized to accept respective hollow cylindrical bolt insulators 51-1 to 51-6 that electrically isolate the clamping bolts from the bottom block 15.

In the center of the O-ring grooves 17A, 17B is a planar upper (fluid channel) face 52 of the lower bottom block 15.

A polymer sheet (also referred to herein as "polymer spacer") 19 is laser cut to define the block separation via its thickness and to provide cutouts 54-1 to 54-6 for the clamping bolts, bottom block electrode cutout 55, an alignment pin cutout 63, and the fluidic flow channel cutout 60.

In general, selection of the specifications and the patterning of his polymer sheet 19 allows rapid prototyping of the fluid channel's key parameters including the channel geometry. For example, the channel geometry includes length, width, height, and profile. These are important both for creating a uniform flow through the channels (e.g. no dead zones) and also for controlling the electrical requirements to achieve a given field (i.e. the current and voltage), repetition rate (relating to residence time and other factors). Additional parameters are electrode separation, fluid residence time (in conjunction with the flow rate), the system resistance to match the impedance range of the power supply, and the surface area to volume (important for boundary layer effects and heat transfer. In the illustrate example, the profile of the channel is narrow at each end with a wider center.

In general, one key feature to be considered when selecting and/or designing polymer sheet 19 concerns the need to form an adequate seal in conjunction with the O-rings used in O-ring grooves 17A, 17B. Another key feature relates to providing a higher dielectric strength relative to that of the fluid, to prevent arcing.

Various materials can be employed to make polymer sheet 19. Examples include but are not limited to elastomers such as polyurethane, silicone or Paralyene (which is the trade name for a variety of chemical vapor deposited poly polymers used as moisture and dielectric barriers). In some cases, the Paralyene formulation selected has a relatively high dielectric strength of greater than 1000 Volts/millimeter and preferably about 7,000 Volts/millimeter.

The polymer sheet may be patterned in areas outside of the O-ring locations (see grove 17B in FIG. 1A) or may form one seating surface of the O-ring seal on the top block. Alternatively, a polymer coating may be patterned directly on the electrode blocks to form the flow channel.

The top block 13 includes a minor arrangement of O-ring grooves to the O-ring grooves 17A, 17B of the bottom block 15 to receive its O-rings OR that engage the top side of the sheet 19. The top block also includes a corresponding array of holes 56-1 to 56-6 that mirror the pattern of the holes 50-1 to 50-6 of the bottom block. The holes 56-1 to 56-6 of the top block 13 are sized to accept respective hollow cylindrical bolt insulators 57-1 to 57-6 that electrically isolate the clamping bolts from the top block 13.

Figure 2A:
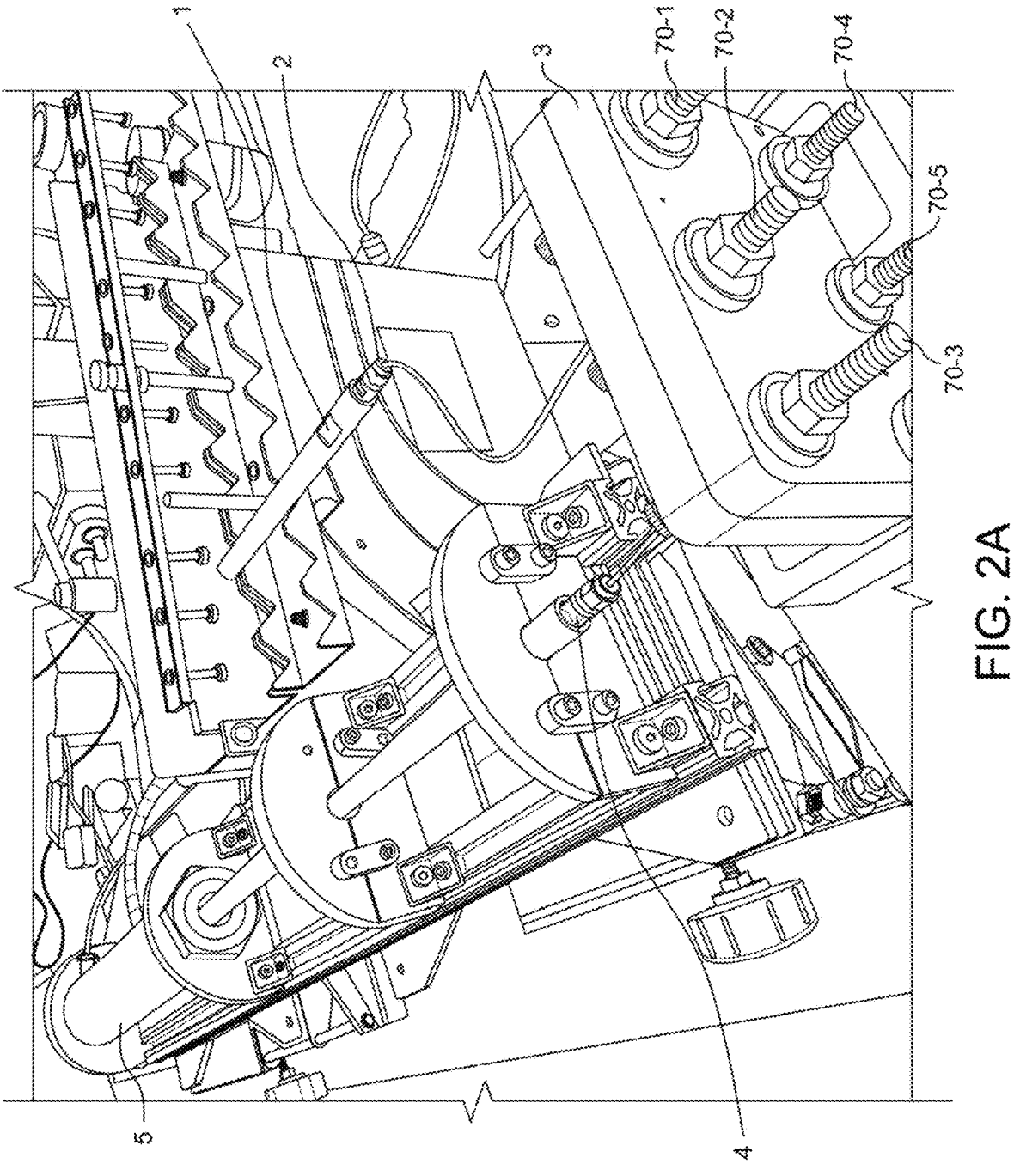
FIG. 2A is an image showing an example of a prototype pumping system used to achieve high pressures with controlled flow rates during electroporation.

Suitable bolts 70-1 to 70-6, see FIG. 2A, extend through the hollow cylindrical bolt insulators 51-1 to 51-6 and bolt insulators 57-1 to 57-6 to clamp together the blocks 13 and 15. Other arrangements, as known in the art, can be used to hold together these blocks while operating at a pressure higher than atmospheric.

The flow channel 21 is laterally defined by the fluidic flow channel cutout 60 formed in the sheet 19. When fully assembled, the bottom of the flow channel is defined by the upper center face of the bottom block, and the top of the flow channel is defined by the lower center face of the top block 13.

Fluid enters the flow channel 21 (a microfluidic channel, for example) through inlet 23 provided by a tube connector 58 that is inserted into through-hole 59 which has been threaded in the top block 13. The through-hole terminates at and opens into the proximal end of the flow channel 21.

Fluid then exits the flow channel 21 through outlet 25 provided by a tube connector 60 that is inserted into a second threaded through-hole 61 in the top block 13 that terminates at and opens into the distal end of the flow channel 21.

The top block 13 and the bottom block 15 are controlled electrically via a top block electrode 31 and a bottom block electrode 33. The top block electrode 31 is pressfit into a blind hole 61 in the top block 13. The bottom block electrode is surrounded by a hollow cylindrical electrode insulator 64 that isolates it from the top block 13. It extends through the top block 13 and through the electrode cutout 55 in the polymer sheet 19. The bottom block electrode 33 makes electrical contact with the bottom block 15 by being press fit into a blind hole 65 formed in the bottom block 15.

In operation, the fluid is exposed to one or more than one permeabilizing electric pulses and then flows out of the device 3 through the outlet 25. Blocks 13 and 15 are charged from a voltage function generator that functions as an electroporation power supply 75 via the electrodes 31 and 33.

FIG. 2A is photograph of a prototype pumping system used to achieve high pressures during electroporation. Referring to FIG. 2A, a programmable syringe pump [1] controls the flow rate from a high pressure stainless steel syringe [2] into the inlet of the electroporation chamber [3]. The outlet of the electroporation chamber is connected to a receiving stainless steel syringe pump [4]. A fixed back pressure is provided by the receiver syringe through the force applied to the syringe plunger by a pneumatic actuator [5] connected to a pneumatic regulator.

This simple system allows both a controlled pressure and a controlled flow rate, both of which are required to allow precise electrical field exposure to the fluid without arcing. A BTX Gemini electroporation power supply and function generator 75 is connected to the electroporation chamber [3] to provide a sequence of electrical pulses at fixed intervals. A custom firmware was developed for the Gemini allowing an unlimited number of pulses to be delivered at programmable pulse rate from 0.1 to 100 seconds, pulse widths of 10-1,000 microseconds, and voltages from 300-3,000 volts. A computer controller 76 with a 12-bit NiDAQ digital to analog converter card 77 measures the voltage across the electrodes and the current through the electrodes using an analog interface 78 that included a series 0.1 Ohm sense resistor allowing the current waveform for each electroporation pulse to be captured for analysis. A three-way ball valve (not shown) can be added to the outlet to allow system sampling filling, rinsing, and purging. The entire wetted path can be sterilized with standard techniques including autoclave, ETO, or gamma irradiation.

Figure 2B:
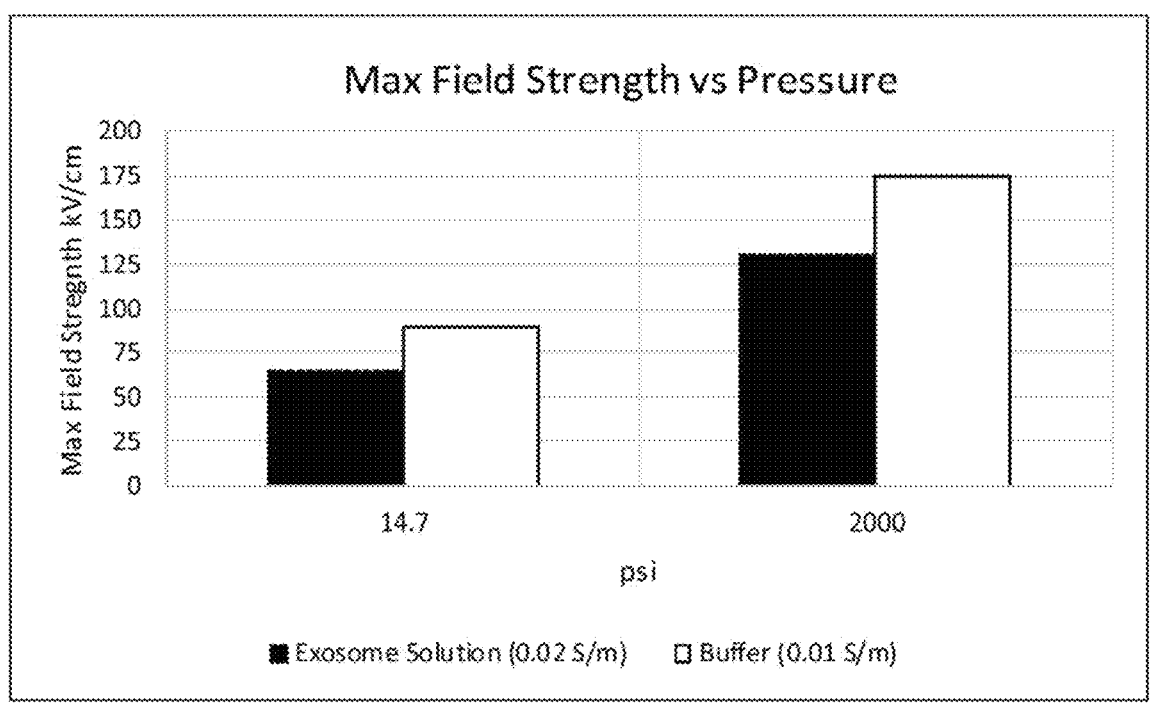
FIGS. 2B and 2C are plots of electric field and current as a function of time showing the maximum electric field and example current traces, respectively, at pressures of 14.7 and 2,000 pounds per square inch (psi).
Figure 2C:
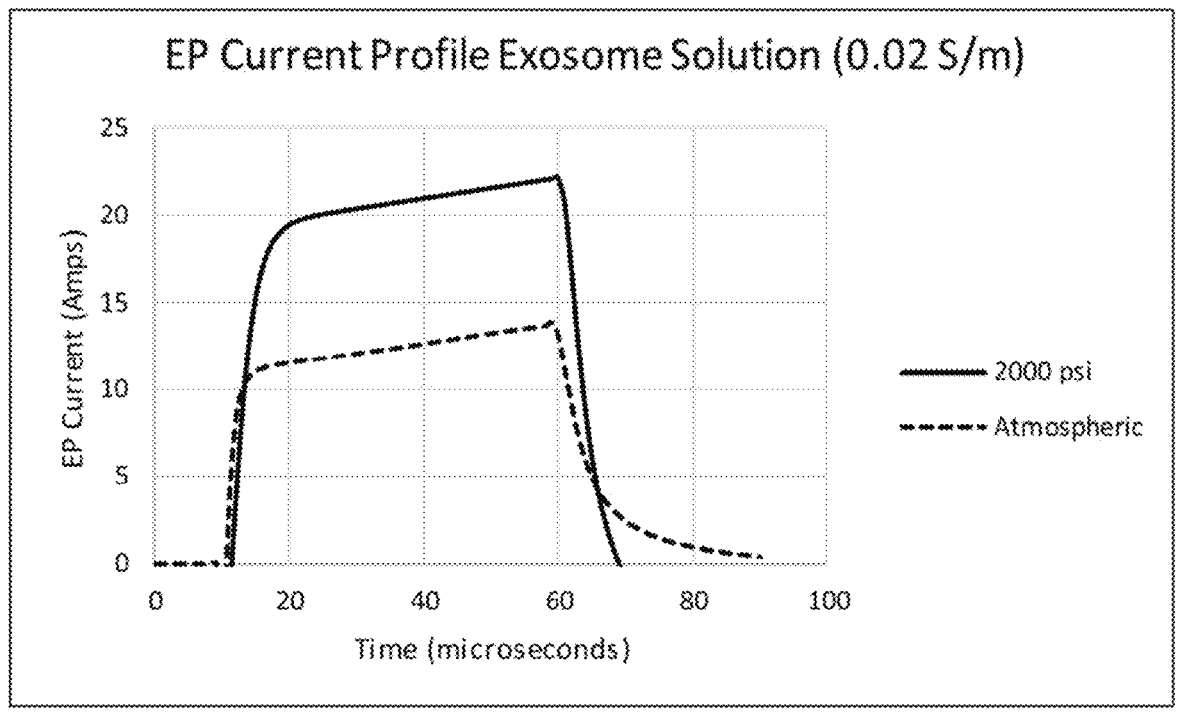

FIGS. 2B and 2C show the maximum electric field and example current traces respectively at 14.7 and 2,000 psi. The conditions for all tests include a 50 microsecond pulse duration at approximately 1 Hz using the exosome solution with a conductivity of 0.02 S/m. The buffer in FIG. 2B has a conductivity of 0.01 S/m. The maximum field strength achievable is inversely related to the solution conductivity; higher conductivities will arc at lower field strengths and deionized water will arc at a significantly higher field strength.

Figure 2D:
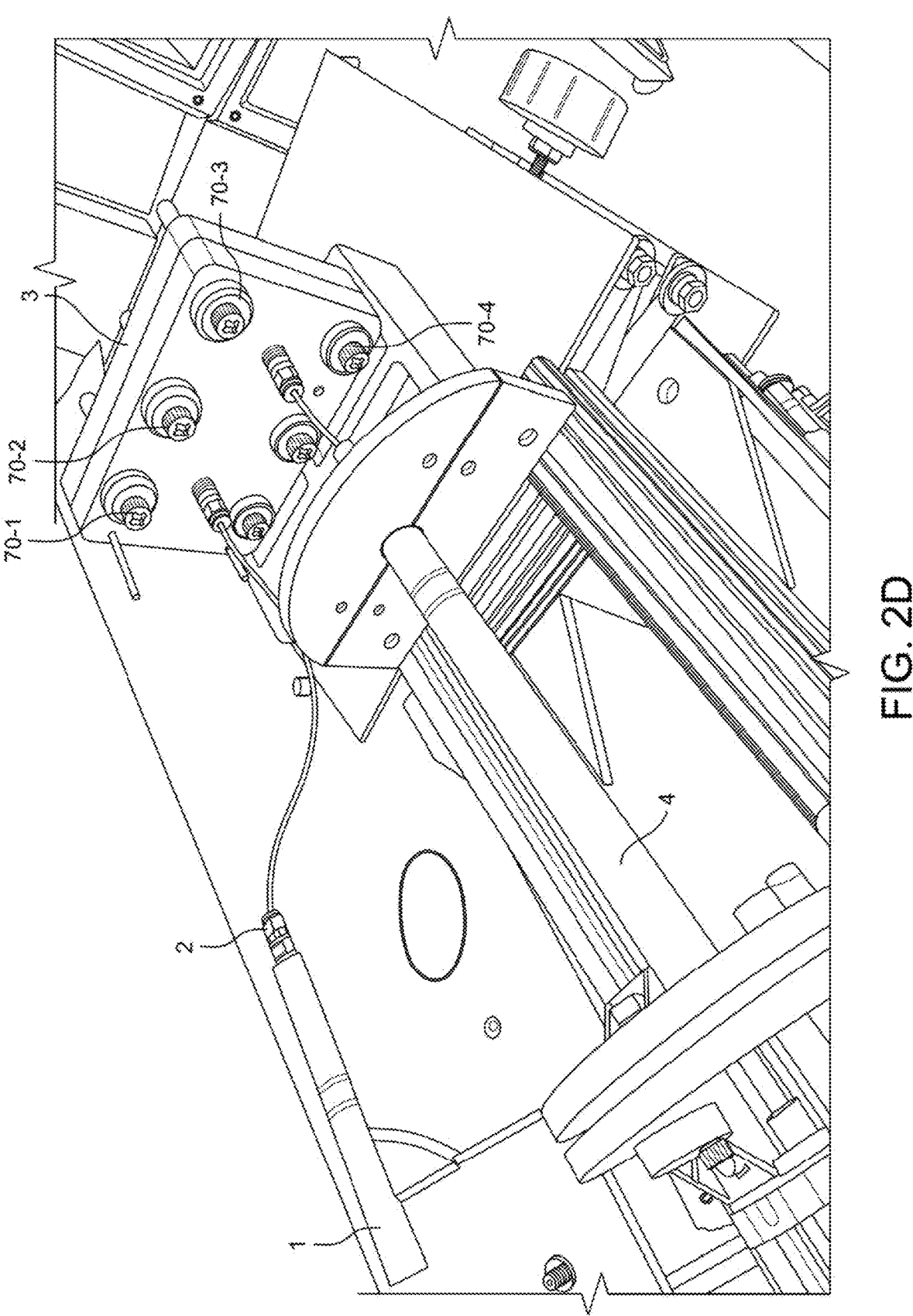
FIG. 2D is an additional image showing the example of the prototype pumping system of FIG. 2A.

FIG. 2D presents a different view of the system in FIG. 2A or sections thereof.

While this system enables proof of concept studies, one skilled in the art could implement a number of alternatives or improvements including having all systems under computer control and synchronization (pumping system, back pressure adjustment, valve control, current monitoring, and electrical pulse control). In situ sensors, such as, for example, fluid pressure sensors, fluid flow sensors, and electrical current sensors to detect pressure, flow and current in the channels and between the electrodes, are further preferably included. Sensors can enable closed loop control over the system.

Other high pressure pumping systems could be used including HPLC (high performance liquid chromatography) pumps with flow rate and pressure sensors for either the inlet and/or the outlet. Alternatively, the inlet and outlet pressure and flow rates could be controlled with high pressure regulators and pressure and flow rate sensors to enable closed loop control.

In general, in the preferred embodiment, the pressure in the flow channel 21 exceeds two atmospheres. Often the pressure is much higher, however, such as higher than 100 psi or 690 kPascals (kPa), and even as high as 1000 psi or 6900 kPA to 2000 psi or 13800 kPa or to as high as 4000 psi or 27600 kPa, or more. Currently 2000 psi is being used. Theoretically, for the dielectric breakdown of water, the higher the pressure the better.

There should be upper limits on the pressure, nevertheless. The upper limit may be dictated by the biology. When exposed to high pressure, many proteins, for example, will denature and/or deactivate. Generally, this occurs at >100 MPa (14,500 psi). Accordingly, the pressure in the flow channels will typically be less than 14,500 psi.

While not shown, a sheath flow can keep the biological entities away from boundary layer/wall effects, resulting in a more uniform residence time in the area undergoing electroporation.

The sheath flow may be planar by for example adding two additional inputs and outputs or an axisymmetric or sheath flows in the vertical as well has horizontal planes can be utilized, resulting in improved residence time uniformity and thus the anticipated transfection uniformity. Axisymmetric and non-axisymmetric arrangements can be implemented in the flow channel or via suitably designed tubing from the pumps. For example, a dual lumen coaxial catheter could be used to create an axisymmetric inner sheath flow surrounding the center biological flow. The sheath flows can have a similar conductivity as the central flow or a different conductivity. For instance, sheath flows with a higher or lower conductivity may be used to direct the field lines optimally through the biologic containing central flow. The optimal sheath composition and geometry can be simulated using COMSOL FEA including fluid mechanics, diffusion, electrophoresis, and electrical field simulations.

Figure 1B:
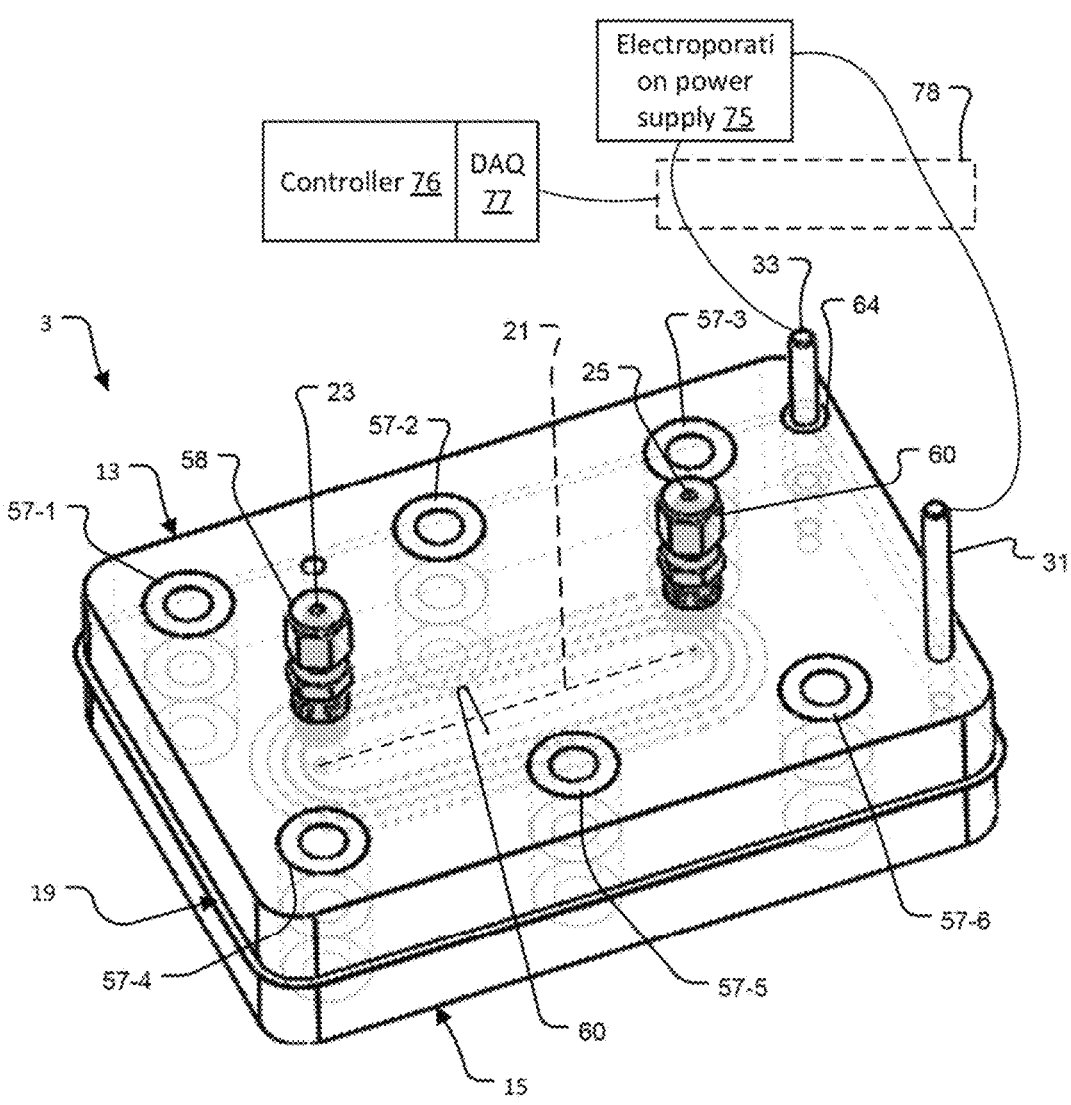

In a device such as device 3 in FIGS. 1A and 1B, sheath flow arrangements can be implemented by adding one or more fluidic inlet(s) and outlet(s), e.g., similar to fluidic inlet 21 and fluidic outlet 23. In some situations, pathways can be formed in the substrate (polymer spacer 19 in FIG. 1A) to connect a sheath inlet to the entrance sections of channel 21 and the sheath outlet to the exiting section of channel 21.

Multiple flow arrangements are described, for example, in U.S. patent application Ser. No. 16/400,270, filed on May 1, 2019 entitled Method and Device for Exosomes Electroporation, which is incorporated herein by this reference in its entirety. One example includes: a central stream, inner sheath streams at either side of the central stream and outer sheath streams at the exterior boundary of the inner sheath streams. In typical arrangements, the center stream fluid (including targets) and the inner sheath fluid (a first buffer, for instance) have a low σ, while the outer sheath fluid (e.g., a second buffer) has a high σ. Another example includes a center stream (target-containing fluid) having a low σ disposed between sheath streams (buffer) having a high σ.

With multiple streams, mixing between streams can be prevented, reduced or minimized by maintaining flows in the laminar regime. While various streams are in physical contact with one another (for transferring cargo to the targets, for instance), flow patterns can be controlled or facilitated by microchannel arrangements configured into the device supporting the flows.

Figure 3:
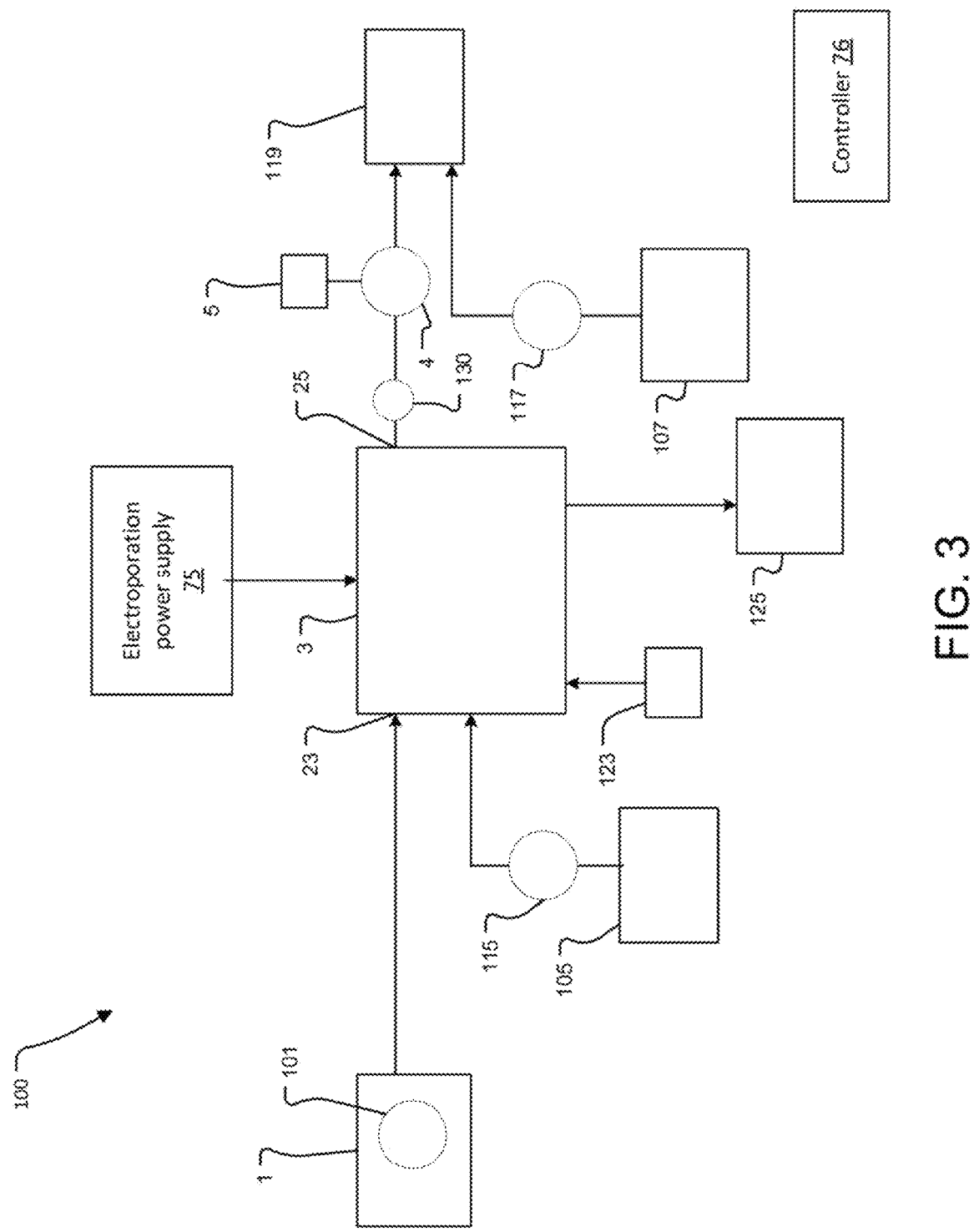
FIG. 3 is a schematic diagram of a system employing a device and pumping system that can be used to achieve high pressures with controlled flow rates during electroporation.

The device and/or pumping system described above can be part of a system such as shown in the schematic diagram of FIG. 3. Shown in this figure is system 100, which includes a reservoir 101 for holding target structures in a suitable culture medium or buffer. In some cases, the reservoir is an incubator. An agitator can be provided to stir the target structures and prevent them from settling. Other fluids that may be needed to conduct a specific process can be supplied from additional reservoirs. The FIG. 3 embodiment shows two illustrative reservoirs, namely upstream reservoir 105 and downstream reservoir 107. More or fewer reservoirs can be employed, however. If needed, reservoirs such as 105 and/or 107 can supply cargo, buffers, washing or rinsing fluids, purging fluids, and so forth. In some cases, the cargo can be provided together with the targets being supplied from fluid reservoir 101.

An input pump 1 (e.g., programmable syringe pump 1 as in FIG. 2A, a HPLC pump or another suitable pump) directs targets-containing fluid from reservoir 101, which is the fluid volume of the syringe of the syringe pump, to electroporation device 3. Typically, the targets are microvesicles or exosomes.

In specific implementations, the electroporation device 3 has the single flow configuration shown in FIGS. 1A and 1B and the target containing fluid is directed to fluidic inlet 23. Electroporation is conducted using electroporation power supply and function generator 75 which produces suitable pulses applied to blocks 13 and 15 via electrodes 31 and 33.

Output fluid is drawn from electroporation device 3 by the receiving syringe 4 or another suitable device. The pneumatic actuator 5 sets the backpressure. In current examples, the backpressure is set to be higher than 100 pounds per square inch or 690 kPa. In some examples, the backpressure is higher than 1000 pounds per square inch or 6900 kPa.

The controller 76 sets and maintains the desired pressure in the electroporation device 3 by controlling the receiving device to set the back pressure in the flow channel 21 of the electroporation device 3.

In general, the receiving device must have compliance to receive fluid at a constant pressure. Other examples include a pressure vessel possibly containing an immiscible fluid to prevent gas from dissolving in the electroporated fluid.

Then the controller 76 sets and maintains the desired flow rate by controlling the input pump to pump against the backpressure at the desired flow rate.

With a fixed backpressure, the controller 76 then operates the pump 1 to provide the desired flow rate while controlling the electroporation power supply 75 to apply the desired voltages across the blocks 13, 15 of the electroporation device 3.

In the single flow configuration of device 3 (FIGS. 1A and 1B) output is drawn from fluidic outlet 25.

Pressure regulators or other approaches for maintaining a desired fluid pressure during electroporation can be employed.

If one or more additional reservoirs are present, each can be provided with its own pump to supply other regents and buffers. In one example, reservoir 105 is provided with pump 115 and reservoir 107 is provided with pump 117.

Output (including, for instance, cargo-loaded target structures, can be collected in reservoir 119, which can be an incubator. In an operation controlled by the controller 76, after the targets are received into the receiving syringe 4, a valve 130 to the device is closed and the controller operates the pneumatic actuator 5 to slowly depressurize the receiving syringe to ambient pressure, then the receiving syringe is actuated to eject the targets into the reservoir 119. If present, sheath fluids can be collected in waste reservoir 125 or directed to an arrangement for recycle. Reservoir 125 also can receive other spent fluids such as washing and/or rinsing solutions.

The system is controlled by controller 76. Often the controller is a microprocessor in a computer system such as a single board computer system. In other cases, the controller is a microcontroller with integrated memory and analog to digital converters and digital to analog converters. In some embodiments, the system is partially or completely automated, with the controller 76 controlling one or more of pumps, incubator conditions, flow patterns, electrical function generator 75, various valves (not shown), such as valves that open or close access to and from various reservoirs, sensors such as sensors 123 comprising one or more probes or detectors for monitoring, setting, adjusting and/or maintaining various parameters such as voltage magnitudes and pulse profiles, temperatures, flow conditions, pressures, incubator conditions, and so forth.

In specific implementations controller 76 receives measurements from various sensors 123 and digitizes these measurements using the analog to digital converter 77 and uses these measurements to adjust process parameters such as flow attributes (rates, residence time, laminar vs. turbulent profile, alignment of the flow streams on their intended path, etc.) In one example, at least one of sensor 123 relies on electrodes suitably placed to allow measurements of the fluid properties (e.g. conductivity or field strength) to optimize the flow parameters in real time of each of the streams individually. Further one or more of sensors 123 can be employed to measure stream temperatures, field strengths during electroporation, pressures, and/or other process parameters of each of the streams, individually.

Operation of the system can be conducted by an optional initial washing or sterilization of device 3. The controller 76 opens valves or energizes the pump 1 and other pumps if additional fluids are employed, to supply central and sheath streams, for example. Controller 76 also activates the electrical function generator 75 which provides an electrical potential across the electroporation electrodes and adjusts process parameters based on preset inputs or commands from the operator or on information received from sensors 123. Product is collected at output reservoir 119 while spent sheath fluids is collected from device 133 and directed to waste reservoir 125 or recycled.

Chosen residence times can vary from 100 microseconds (μs) to about a second. An AC (for example, sinusoids or pulse trains with periods/pulse widths ranging from 10 ns to 100s of microseconds) or DC electric field is established and remains active while targets flow through the device. The magnitude of the field is tuned for the specific type of target to a value sufficient to achieve permeabilization. In specific examples, the field is in the range of 100-30,000 kV/m.

Suitable conductivity values for the central fluid can be within the range of from about 0.1 to about 0.01 S/m (Siemens per meter).

In addition, the low conductivity fluid minimizes Joule heating, an important consideration for biologics. The temperature rise due to joule heating is given by:

$$\Delta T_1 = \frac{\sigma_0 V_0^2 t_p}{\rho c d^2}$$

where $\sigma_0$ is the conductivity, $V_0$ is the applied voltage, $t_p$ is the pulse duration, $\rho$ is the fluid density, c is the heat capacity and d is the gap between the electrodes. Joule heating in this case is directly proportional to the solution conductivity.

Use of microfluidic flow allows convective transport of heat generated via Joule heating.

Another characteristic of some of the microfluidic approaches described herein involves electrodes that are remote from the biological entities. By keeping the electrodes far from the biological entities relative to diffusional length/time scales, potentially damaging Faradaic by-products (oxygen, hydronium, chlorine, free radicals) cannot interact with the biological entities nor can the biological entities undergo direct redox reactions at the electrodes.

In general, higher field strengths are reached by minimizing the generation of arc nucleating vapor bubbles at the electrodes. This can be accomplished by several strategies. In one embodiment, the fluid is maintained under a high pressure (1-1,000 bar) which prevents bubbles from nucleating and collapses any existing air bubbles. Also minimizing the current required to generate a given field and/or by spatially controlling the field strengths can reduce arcing from air bubbles. In some implementations, the current is minimized by using one or more low conductivity fluids to simultaneously minimize gaseous electrolysis products (Faraday's law), while also minimizing Joule heating which can lead to local boiling. Additionally, by minimizing the field strength in the vicinity of the electrodes, any bubbles that do form are less likely to initiate an arc by exceeding the vapor dielectric breakdown voltage (~30 kV/mm in air).

Further embodiments described herein relate to mitigating the formation of bubble, via electrolysis products, for example. Various techniques can be employed. One approach relies on degassing the fluid e.g., in the region where the electrodes reside, to dissolve or prevent nucleation of gaseous electrolysis by-product.

Another approach relies on the electrode capacitance (e.g. higher electrode surface area) thereby operating in a capacitive mode and minimizing or eliminating Faradaic current. In turn, electrode surface area can be increased by: increasing electrode nominal size; increasing electrode effective electrochemical area by roughening the target; depositing nanoclusters in vapor phase; or by electrochemically depositing rough films (e.g. platinum black).

Current can also be capacitively coupled through a non-conductive sheath fluid. In this case, metal electrodes could charge a thin non-conductive sheath fluid which is in communication with the central flow. For example, ethylene glycol is a high dielectric constant non-conductive fluid. Alternatively, the non-conductive sheath flow could be immiscible with the central flow such as an oil phase.

Other approaches for controlling bubbles use PEDOT (PSS or poly(3,4-ethylenedi-oxythiophene) polystyrene sulfonate) or other conducting polymer or metal (e.g., Ag) that undergoes Faradaic charge transfer.

Sense electrodes can be placed within the outer, inner, or central flows to make relevant measurements (e.g. conductivity, temperature, field strength measurements). These electrodes may provide real time feedback to adjust the operational parameters during electroporation. As an example, an RTD electrode may be placed in the central flow to monitor the temperature excursion of the biologics. A further example may include placing electrodes to measure the conductivity of the sheath and central flows at the outlet to allow non-visual alignment of the flows to the intended outlets and to make sure there is not excessive mixing of the flows. A further example may include placing opposing electrodes across the central flow to measure the potential difference thereby estimating the field strength in the central flow.

Operationally, the pressure and fluid velocities can be nominally matched at the stream interfaces; having separate outlets for each fluid allows the pressure drop to the outlet for each flow stream to be independently tuned to prevent the fluid streams from deforming and/or deflecting. Additionally, common inlets for sheath flows can be undesirable in terms of creating electrical leak paths by providing competing electrical paths with the intended electrical path across the central fluid.

In some cases, flows can be visualized to allow parameters to be tuned in real time using tracers or imaging the biological entities if transparent electrode blocks are used (e.g. transparent plastic or glass with patterned electrodes. Alternatively, electrodes can be placed locally at the beginning and end of the flow channels to allow measurements of the fluid properties (e.g. conductivity or field strength) to optimize the flow parameters in real time such that fluid paths remain aligned to the intended flow paths. This tuning can be passive by designing channel geometries or outlet tubing with the appropriate diameters and lengths or by actively applying pressures using a chamber with a pressure controller.

In some cases, target structures can be driven, e.g., acoustically, from one buffer to another by performing buffer exchanges such as described, for example, in U.S. patent application Ser. No. 16/359,626, filed on Mar. 20, 2019, entitled Acoustically-Driven Buffer Switching for Micropar-ticles, or U.S. patent application Ser. No. 16/557,820 filed on Aug. 30, 2019, entitled Method and Apparatus for High Throughput High Efficiency Transfection of Cells, both being incorporated herein by reference in their entirety.

Implementations of the invention can be practiced or adapted to reagent-based methods such as delivery by lipids (e.g. transfectamine), calcium phosphate precipitation, cat-ionic polymers techniques, DEAE-dextran, magnetic beads, virus-based approaches, and other applications.

While this invention has been particularly shown and described with references to preferred embodiments thereof, it will be understood by those skilled in the art that various changes in form and details may be made therein without departing from the scope of the invention encompassed by the appended claims.

What is claimed is:

1. An electroporation system comprising:
an electroporation device comprising a flow channel and a pair of electrodes, the electroporation device com-prising a conductive material configured to apply an electric field to the flow channel in response to a voltage applied across the pair of electrodes;
a voltage generator electrically coupled to the pair of electrodes and configured to apply the voltage across the pair of electrodes;
a pump fluidly coupled to the flow channel, the pump configured to direct a fluid through the flow channel and configured to generate a pressure of two atmo-spheres or greater in the fluid within the flow channel; and
a controller operably coupled to the voltage generator and the pump, the controller configured to operate the pump to direct the fluid through the flow channel and generate the pressure in the fluid within the flow channel, the controller further configured to simultaneously operate the voltage generator to apply the voltage across the pair of electrodes to apply the electric field to the fluid while the fluid is at the pressure of two atmospheres or greater within the flow channel.

2. The electroporation system of claim 1, wherein the pressure is higher than 100 pounds per square inch or 690 kPa.

3. The electroporation system of claim 1, wherein the pressure is higher than 1000 pounds per square inch or 6900 kPa.

4. The electroporation system of claim 1, wherein the pump comprises a syringe pump.

5. The electroporation system of claim 4, further com-prising a receiver device for controlling back pressure in the flow channel.

6. The electroporation system of claim 1, wherein the electroporation device comprises a top block, a bottom block, and a dielectric spacer separating the top block and the bottom block.

7. The electroporation system of claim 6, wherein the blocks have a thickness that is greater than 5 millimeters.

8. The electroporation system of claim 6, wherein the dielectric spacer comprises a flow channel cutout in the spacer for defining lateral sides of the flow channel.

9. The electroporation system of claim 6, wherein a profile of the flow channel is narrow at each end with a wider center.

10. The electroporation system of claim 6, wherein the dielectric spacer has a dielectric strength of greater than ~1,000 Volts/millimeter.

11. The electroporation system of claim 1, further com-prising a reservoir upstream of the flow channel, wherein the reservoir is configured to contain the fluid.

12. The electroporation system of claim 11, further com-prising the fluid in the reservoir, the fluid comprising an electroporation target material and a cargo material.

13. The electroporation system of claim 12, wherein the electroporation target material comprises at least one vesicle, at least one microvesicle, and/or at least one exo-some.

14. The electroporation system of claim 11, wherein the pump is a syringe pump and the reservoir comprises a fluid volume of a syringe of the syringe pump.

15. The electroporation system of claim 6, wherein at least one of the top block and the bottom block comprises the conductive material.

16. The electroporation system of claim 1, wherein the pump is further configured to direct the fluid through the flow channel at a desired flow rate, and the controller is configured to direct the fluid through the flow channel at the desired flow rate while controlling the voltage generate to apply the voltage to the electroporation device.

17. The electroporation system of claim 1, wherein the pump is configured to direct the fluid through the flow channel at a pressure of 2000 pounds per square inch or greater.

18. The electroporation system of claim 1, wherein the controller comprises a microprocessor or a microcontroller.

* * * * *